US006488205B1

(12) United States Patent
Jacobson

(10) Patent No.: US 6,488,205 B1
(45) Date of Patent: Dec. 3, 2002

(54) SYSTEM AND METHOD FOR PROCESSING DATA ON AN INFORMATION CARD

(76) Inventor: Howard John Jacobson, 11510 Cushman Rd., Rockville, MD (US) 20852

( * ) Notice: Subject to any disclaimer, the term of this patent is extended or adjusted under 35 U.S.C. 154(b) by 0 days.

(21) Appl. No.: 09/453,206

(22) Filed: Dec. 3, 1999

(51) Int. Cl.[7] .................................................. G06K 5/00
(52) U.S. Cl. ............................. 235/380; 705/2; 705/3
(58) Field of Search ................................. 235/375, 380, 235/382; 705/1–4

(56) References Cited

U.S. PATENT DOCUMENTS

| 4,817,166 A | 3/1989 | Gonzalez et al. ............ 382/105 |
| 4,931,950 A | 6/1990 | Isle et al. ....................... 705/11 |
| 4,949,388 A | 8/1990 | Bhaskaran ................... 382/159 |
| 5,208,745 A | 5/1993 | Quentin et al. ................ 700/83 |
| 5,254,860 A | 10/1993 | Yeh et al. ..................... 250/566 |
| 5,264,933 A | 11/1993 | Rosser et al. ................ 348/578 |
| 5,347,477 A | 9/1994 | Lee ............................. 708/141 |
| 5,349,210 A | 9/1994 | Ackley et al. .................. 257/84 |
| 5,374,999 A | 12/1994 | Chuang et al. .............. 358/496 |
| 5,483,052 A | 1/1996 | Smith, III et al. ....... 235/462.49 |
| 5,493,105 A | 2/1996 | Desai ........................... 235/379 |
| 5,600,756 A | 2/1997 | Ely ............................ 704/235 |
| 5,604,640 A | 2/1997 | Zipf et al. .................... 359/803 |
| 5,642,442 A | 6/1997 | Morton et al. .............. 382/287 |
| 5,666,492 A | * 9/1997 | Rhodes et al. .................. 705/3 |
| 5,688,173 A | 11/1997 | Kitahara et al. .............. 463/29 |
| 5,724,575 A | * 3/1998 | Hoover et al. .............. 395/610 |
| 5,748,807 A | 5/1998 | Lopresti et al. ............. 382/310 |
| 5,748,973 A | 5/1998 | Palmer et al. .................. 704/9 |
| 5,761,328 A | 6/1998 | Solberg et al. ............. 382/113 |
| 5,799,190 A | 8/1998 | Lynch et al. ................ 435/7.93 |
| 5,845,261 A | 12/1998 | McAbian ...................... 705/26 |
| 5,846,131 A | 12/1998 | Kitahara ....................... 463/29 |
| 5,852,434 A | 12/1998 | Sekendur .................... 345/179 |
| 5,890,129 A | * 3/1999 | Spurgeon ........................ 705/4 |
| 5,930,759 A | * 7/1999 | Moore et al. ................... 705/2 |
| 6,067,522 A | * 5/2000 | Warady et al. ................. 705/2 |
| 6,082,776 A | * 7/2000 | Feinberg ...................... 283/72 |
| 6,088,695 A | * 7/2000 | Kara ........................... 707/10 |
| 6,092,047 A | * 7/2000 | Hyman et al. .................. 705/1 |
| 6,112,986 A | * 9/2000 | Berger et al. ............... 235/380 |

FOREIGN PATENT DOCUMENTS

JP         2001063255 A   *  3/2001

OTHER PUBLICATIONS

Network Services End User Training manual, Medical Manager Corporation, Version 9 MMNS 2.10 Jan. 1999.

(List continued on next page.)

Primary Examiner—Thien M. Le
Assistant Examiner—Jamara A. Franklin
(74) Attorney, Agent, or Firm—Andrea G. Reister; Covington & Burling

(57) ABSTRACT

The present invention is directed toward a system and method for extracting and processing data contained on an information card, particularly a healthcare plan identification card. The data preferably includes both textual data and graphical data, but can contain either type of data singularly. The system preferably associates the textual and graphical data or a portion thereof with a healthcare plan sponsor. In addition, the system analyzes the data to determine a healthcare plan product identifier. Based upon the healthcare plan product identifier, the system provides information about the healthcare plan product so that decisions can be made about an individual associated with the healthcare plan product.

15 Claims, 6 Drawing Sheets

OTHER PUBLICATIONS

PC Magazine vol. 19 No. 2, Jan. 18, 2000, p. 57.

Computer Shopper.com, *OCR Gets Down to Business Cards*, (originally published in Nov. 1996 issue), <<http://www.zdnet.com/computershopper/edit/cshopper/content/9611/cshp0155.html>>, visited Jun. 24, 1999.

Doermann, D., Rivlin, E., & Weiss, I., *Applying algebraic and differential invariants for logo recognition*, Machine Vision and Applications, 9:73–86 (1996).

EDT Business Card Reader: Biz Card Manager 4.0, <<http://www.edti.com/bcm40.htm>>, <<http://www.edti.com/mainmenu.htm>>, both visited Jun. 23, 1999.

Tessler, Franklin, *Business Card Scanners,* Macworld Online, Apr. 1996, <http://macworld.zdnet.com/pages/april.96/reviews.1959.html>>, visited Jun. 24, 1999.

Optical Character Recognition Technology, <<http://www.the-fbc.org/ocr.html>>, visited Jun. 24, 1999.

EasyRoad OCR Software, Pictronics, <<http://www.pictronics.com/er.htm>>, visited Jun. 2, 1999.

* cited by examiner

PATIENT INSTRUCTIONS: THIS IS YOUR HEALTH PLAN IDENTIFICATION CARD. PRESENT IT TO THE PROVIDER OF HEALTH CARE WHEN YOU OR YOUR ELIGIBLE DEPENDENTS RECEIVE SERVICES. PRE-HOSPITAL REVIEW: BEFORE ANY NON-EMERGENCY HOSPITAL ADMISSION (OR WITHIN 48 HOURS IF EMERGENCY) CALL THE WECARE HEALTHSYSTEMS NUMBER ON THE BACK OF THIS CARD PRIOR TO CERTIFICATION OF HOSPITAL ADMISSIONS OR YOUR BENEFITS WILL BE AFFECTED. FOR PRE-CERTIFICATION CALL: 1-800-999-9999.

PRO PROVIDER INSTRUCTIONS: FOR PRIOR CERTIFICATION OF HOSPITAL ADMISSIONS CALL THE WE CARE HEALTH SYSTEMS CUSTOMER SERVICE NUMBER SHOWN ON THE FRONT OF THIS CARD.

IN-NETWORK PROVIDERS MAIL CLAIMS TO: IN NETWORK, P.O BOX 001, WASHINGTON, D.C. 20004
ALL OTHER PROVIDERS MAIL CLAIMS TO: OUT NETWORK, P.O. BOX 100, BALTIMORE, MD 43032
DENTAL PROVIDERS MAIL CLAIMS TO: DENTAL NETWORK, 343 HUCK STREET, LARGO, MD 22312

WECARE HEALTHSYSTEMS

*FIG. 3B*

SYSTEM AND METHOD FOR PROCESSING DATA ON AN INFORMATION CARD

BACKGROUND OF THE INVENTION

1. Field of the Invention

The present invention relates generally to optical electronic systems and methods. More particularly, the present invention relates to systems and methods for facilitating decision making about an individual based on mixed media information cards.

2. Related Arts

The use of information or identification cards has seen increasing use over the past several years as an effective means for quickly identifying an individual and a group or company with whom the individual is associated. Perhaps no industry has witnessed a more explosive growth in the use of these information cards than has the healthcare industry.

In the healthcare industry, healthcare sponsors, such as insurance companies, generally issue an information card, or healthcare plan identification card, to individuals in order to show that the individual is insured and to provide a variety of information about the individual and the individual's insurance coverage. Conventionally, these cards have been presented to front office staff working, for example, in a doctor or dentist office when the individual arrives for an appointment. In conventional systems and methods, the front office staff manually enters the information contained on the card into a data gathering system, such as a patient log or computer database. Such information can include the name of the healthcare sponsor or the insurance company and personal information about the individual, including, but not limited to, the individual's name, social security number or other individual numeric identifier, and the individual's employer. This information is then used to generate bills or invoices or to provide additional information to the healthcare sponsor.

The conventional methods for entering and handling the information contained on the identification or business cards have presented numerous problems. These methods have generally not been capable of tracking and/or keeping up with changes of individual healthcare plans chosen by employers for their employees and the creation and marketing of new products by healthcare sponsors. In addition, the conventional methods have also resulted in incorrect information being entered into the computer system, which has led to incorrect billing of the healthcare sponsor, including billing the wrong address and incorrect collection of a co-pay amount from an individual at the time services are rendered. Another problem with conventional systems and methods has been that front office staff working in the office do not always follow the special utilization management requirements the healthcare sponsor may have, such as, obtaining precertification of certain outpatient procedures. Failure to follow these special procedures has resulted in loss of revenue to the doctor as well as administrative delays in providing insurance coverage. Yet another problem with conventional systems and methods has been front office staff cannot always determine if a particular physician participates in a plan. Such information is important in determining if the patient is within the plan's network of approved physicians, outside the plan's network of approved physicians, or not covered at all.

Various business card scanning systems have been developed for scanning business cards and storing the information printed on the business cards in an electronic database. The electronic database can then later be used to retrieve information about a particular individual or company. This retrieval process is similar to the conventional rolodex systems except that it can be performed electronically. Such scanning systems, however, are limited to extracting the data from the information cards and storing that data in the electronic database. Such conventional systems do not overcome the problems associated with healthcare sponsor identification cards.

Thus, there is a need to overcome the disadvantages described above. There is a particular need to provide a system and method that simply and reliably reads information contained on information cards to simplify the decision making process for front office staff and eliminate data input errors associated with conventional systems. There is a particular need for an automated system that reads information from insurance identification cards and identifies a healthcare sponsor and any special administrative procedures associated with the sponsor. There is a further need for storing information contained on the identification cards so that this information can be updated easily in cases of insurance coverage changes or other similar changes to group or healthcare sponsor offerings.

SUMMARY OF THE INVENTION

The present invention solves the problems with, and overcomes the disadvantages of, conventional information card management systems.

The present invention relates to a method for processing data contained on an information medium, the information medium being associated with an individual. The method includes extracting the data from the information medium and analyzing the data to determine a group identifier, wherein the group identifier identifies the individual as part of a group. The method further includes analyzing the data to determine a group product identifier and providing group product information based on the group product identifier.

In another aspect, the present invention relates to a system for processing data contained on an information medium associated with an individual. The system includes a scanner which is configured to extract data from the information medium. The system further includes a computer system in data communication with the scanner. The computer system includes a processor configured for analyzing the data to determine a group identifier, wherein the group identifier identifies the individual as part of a group, analyzing the data to determine a group product identifier, and providing group product information based on the group product identifier.

The present invention also relates to a computer program product including a computer useable medium having computer program logic recorded thereon for enabling a processor in a computer system to process data contained on an information medium. The computer program product includes first analyzing means for enabling the processor to analyze the data to determine a group identifier, wherein the group identifier identifies the individual as part of a group. The computer program also includes second analyzing means for enabling the processor to analyze the data to determine a group product identifier. The computer program further includes providing means for enabling the processor to provide group product information based on the group product identifier.

In another aspect, the present invention relates to a system for processing data contained on an information card associated with an individual. The system includes means for extracting the data from the information card and first means for analyzing the data to determine a group identifier, wherein the group identifier identifies the individual as part of a group. The system also includes second means for analyzing the data to determine a group product identifier and means for providing group product information based on the group product identifier.

The present invention also relates to a method for processing data contained on an identification card issued by a healthcare plan sponsor. The method includes extracting data from the identification card and analyzing the data to determine a healthcare plan identifier. The method also includes analyzing the data to determine a healthcare plan product identifier and providing healthcare plan product information based on the healthcare plan product identifier.

In another aspect, the present invention relates to a system for processing data contained on an identification card issued by a healthcare plan sponsor. The system includes a memory device having embodied therein executable code and a processor in communication with the memory device. The processor is configured for extracting data from the identification card and analyzing the data to determine a healthcare plan identifier. The processor is further configured for analyzing the data to determine a healthcare plan product identifier and providing healthcare plan product information based on the healthcare plan product identifier.

The present invention also relates to a computer program product including a computer useable medium having computer program logic recorded thereon for enabling a processor in a computer system to process data contained on an identification card issued by a healthcare plan sponsor. The computer program includes first analyzing means for enabling the processor to analyze the data to determine a healthcare plan identifier and second analyzing means for enabling the processor to analyze the data to determine a healthcare plan product identifier. The computer program also includes providing means for enabling the processor to provide healthcare plan product information based on the healthcare plan product identifier.

In yet another aspect, the present invention relates to a system for processing data contained on an identification card issued by a healthcare plan sponsor. The system includes means for extracting data from the identification card and a first means for analyzing the data to identify a healthcare plan identifier. The system also includes a second means for analyzing the data to identify a healthcare plan product identifier and means for providing healthcare plan product information based on the healthcare plan product identifier.

Features and Advantages

A feature of the present invention is that it provides for a reliable and efficient method and system capable of tracking and/or keeping up with changes to individual healthcare plans that are chosen by employers for their employees.

An additional feature of the present invention is that it provides for a simple system and method for accepting the creation and marketing of new products by healthcare sponsors.

Yet another feature of the present invention is that it provides for automated extracting and entry of data contained on information media and the subsequent analysis of that data based on previously stored information or information obtained directly from a healthcare sponsor.

An advantage of the present invention is that it substantially eliminates the manual entry techniques of conventional systems and the possibility of incorrect information being entered into the computer system, which has, in the past, led to incorrect billing of the healthcare sponsor.

Another advantage of the present invention is that it notifies front office staff of any special utilization management requirements the healthcare sponsor may have, such as, obtaining precertification of certain outpatient procedures. In this fashion, the present invention helps to simplify decisions for front office staff and helps to curb the loss of revenue to the doctor and the loss of time due to administrative delays inherent in conventional systems.

BRIEF DESCRIPTION OF THE DRAWINGS

The accompanying drawings, which are incorporated in and constitute a part of this specification, illustrate embodiments of the invention and, together with the description, serve to explain the features, advantages, and principles of the invention.

FIG. 3b illustrates exemplary information contained on information cards suitable for use in the present invention;

DETAILED DESCRIPTION

Overview

The present invention is directed toward a system and method for extracting and processing data contained on an information medium. Exemplary information media include, but are not limited to, an identification card, a facsimile copy or photocopy of the identification card, any suitable information card or facsimile copy or photocopy of the same, or an electronic version of any of the foregoing. The electronic version may be stored in a computer memory or other type of computer-readable medium, such as, but not limited to, a diskette, or CD-ROM. It should be understood by one of ordinary skill in the art that the present invention relates to a plurality of healthcare plans, such as, but not limited to, medical, dental, vision care, pharmacy, or the like. In addition, the present invention is not limited to healthcare plan identification cards, and can include, rewards cards associated with airlines or telecommunications companies or any other suitable form of information media.

The data preferably includes both textual and graphical data, but can contain either type of data singularly. The system preferably associates the textual and graphical data or a portion thereof with a healthcare plan sponsor. In addition, the system analyzes the data to determine a healthcare plan product identifier. Based upon the healthcare plan product identifier, the system provides information about the healthcare plan product so that decisions can be made about an individual associated with the healthcare plan product.

System and Method of the Present Invention

Figure 1:
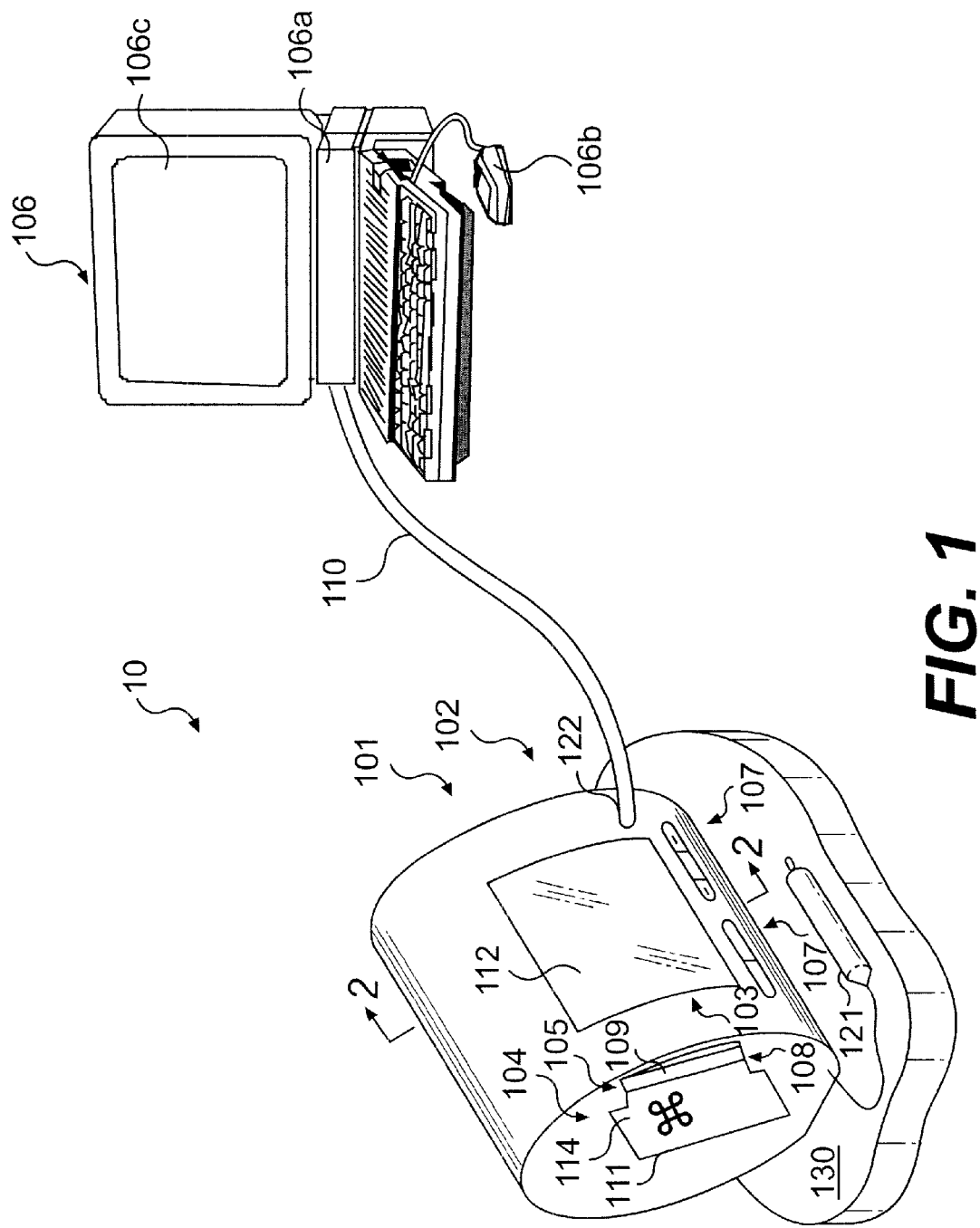
FIG. 1 is a perspective view of an exemplary embodiment of the system of the present invention.

An exemplary embodiment 10 of the present invention is shown generally in FIG. 1. As can be seen from FIG. 1, the present invention preferably includes a scanning system 101 and a computer 106 including a computer processor and memory storage area 106a coupled to scanning system 101. In the exemplary embodiment, the medium comprises an information card 111. Accordingly, scanning system 101 can be alternately referred to as information card scanning system 101.

Computer 106 includes an input device 106*b,* such as a keyboard, mouse, or other suitable device and a display device 106*c.* A data communication link 110 preferably couples card scanning system 101 and computer 106. Communication link 110 is preferably configured to transmit data from scanning system 101 to computer 106 and from computer 106 to scanning system 101.

An exemplary scanning system 101 suitable for use in the present invention is shown and described in detail in U.S. Pat. No. 5,604,640, which is herein incorporated by reference in its entirety.

As shown in FIG. 1, card scanning system 101 is illustrated having a portion 105 thereof broken away and resting on a substrate 130, such as a desk, table, or the like. It should be understood that card scanning system 101 in the embodiment depicted in FIG. 1 is a desk top model; however, card scanning system 101 is capable of being utilized as a hand held unit. Card scanning system 101 preferably includes several major components, such as a hollow body 102, apertures or openings 103 and 104, a plurality of control keys or function keys 107, and a data scanning system 108. Additionally, as is also shown in FIG. 1, an exemplary information card 111 is illustrated in part. It should be apparent to one having ordinary skill in the art that information card 111 can include business cards, healthcare plan identification or insurance cards and the like. Examples of these information cards will be discussed in more detail below with reference to FIG. 3*a.*

Hollow body 102 is made of any suitable well-known material in the art, such as plastic, metal, resin, or the like, as well as being formed by any suitable well-known method in the art such as molding, injection molding, milling, or the like. Further, it should be understood that hollow body 102 may be made of more than one piece, thus enabling a multiple piece hollow body 102 to be constructed. In an exemplary embodiment of the present invention, hollow body 102 is injection molded with plastic molding materials, as well as having a plurality of pieces that are interlocked together.

The plurality of function keys or control keys 107 are located on hollow body 102 for easy access and use. The plurality of function keys or control keys 107 allow a user to access a variety of controls, such as positioning information card 111, displaying information card 111, scanning information card 111, displaying a previously scanned information card 111, and sorting routines that enable the user to organize the previously scanned information cards 111. Generally, sorting routines are performed utilizing any suitable method, such as alphabetic, numeric, name, or the like. Alternatively, the sorting routines and other information management can be performed on computer 106 coupled to card scanning system 101. The plurality of control keys 107 are made and installed in hollow body 102 by well-known methods in the art. Further, it should be understood that the plurality of control keys 107 are preferably operably connected to computer 106 or processing center, described hereinafter, via communication link 110.

Opening 103 provides a viewing port 112 to enable the user to directly perceive or view information card 111, to directly perceive or view an enlargement of information card 111, or to directly perceive or view a representation of a previously scanned information card 111. By way of example only, direct viewing of information card 111 is achieved by moving information card 111 under viewing port 112 and having viewing port 112 made of a non-refractive and non-diffractive element, such as a transparent piece of plastic. Alternatively, information card 111 is enlargeable by using optical elements, such as a refractive optical element, a diffractive optical element, or combination thereof. Use of refractive and diffractive optical elements in viewing port 112 enables the user to obtain a substantial amount of eye relief, thereby enabling the user to perceive or view information card 111 with ease and comfort.

Information card 111 is made utilizing any suitable encoding technology, such as paper print technology, magnetically encoding technology, bar encoding technology, or the like. Each of these technologies can either be utilized singly or in combination with each other, thereby enabling information card 111 to have a mixed media format which is custom tailored to individual applications. For example, with information card 111 being made of a plastic material utilizing print or graphic technology, as well as utilizing magnetic encoding technology, surface 114 of information card 111 expresses graphical and textual images (e.g., a logo associated with a group or healthcare plan sponsor, telephone, address, and the like), while the magnetic encoding of information card 111 enables a list of healthcare plans and their associated specifications to be encoded into information card 111, thereby enabling the owner of the information card 111 to more effectively communicate, for example, his insurance coverage to a front office staff working in a doctor office. Additionally, it should be understood that mixing the various encoding technologies into information card 111 enables information card 111 to be more flexible in function than the conventional information cards used today.

Sensor system 108 utilizes any suitable technology or any combination of technologies, such as optical technologies, magnetic technologies, or the like. For example, with scanning system 108 using optical technology, a sensor 109 is preferably a photosensor or a photodiode that detects information depicted or embedded on information card 111 as information card 111 passes by sensor 109. Further, it should be noted that additional sensors can be added to information card scanning system 101 so as to detect a variety of encoded information on information card 111.

By way of example only, with scanning system 108 being a photo scanning system, sensor 109 typically includes any suitable photodetector array having photodiodes, pin photodiodes, or the like. As information card 111 passes by sensor 109, graphical and textual information is sensed by sensor 109 and converted into electrical signals. The electrical signals are subsequently sent to electronics 201 (shown in FIG. 2) for processing, storage, and the like, or subsequent transfer to computer 106.

Additionally, a light pen 121 may be incorporated into information card scanning system 101 as an alternative method for transmitting data from information card 111 into information card scanning system 101. In this embodiment, data is encoded on information card 111 in a bar code format. Light pen 121 is moved across the bar codes on information card 111, thereby transmitting the data from the bar codes through light pen 121 and into the electronics (shown in FIG. 2) in information card scanning system 101.

Further, an accessory port 122 provides a method to integrate or couple information card scanning system 101 to a variety of electronic accessories, such as a personal digital assistant (PDA) (not shown), computer 106 via communication link 110, and the like.

In another exemplary embodiment of the present invention, the information medium comprises a facsimile copy or a photocopy of information card 111. In such an embodiment, a flatbed scanner (not shown), which is known in the art, may be incorporated into or coupled to scanning system 101 as an alternative method for transmitting data from the facsimile copy or photocopy of information card 111. In this embodiment, the data, as described above, is scanned from the facsimile copy or photocopy, converted into electrical signals, and subsequently sent to electronics 201 (shown in FIG. 2) for processing, storage, and the like, or subsequent transfer to computer 106.

In yet another exemplary embodiment of the present invention, data pertaining to an individual patient can be sent directly to computer 106 via, for example, electronic mail, or other suitable mode of electronic communications. A computer program residing on computer 106 would extract the data from the electronic mail message and store the information for later use. In yet of further embodiment of the present invention, an individual, such as the front office staff member, could manually enter the data from any of the information media directly into computer 106 via, for example, a computer program residing on computer 106.

Figure 2:
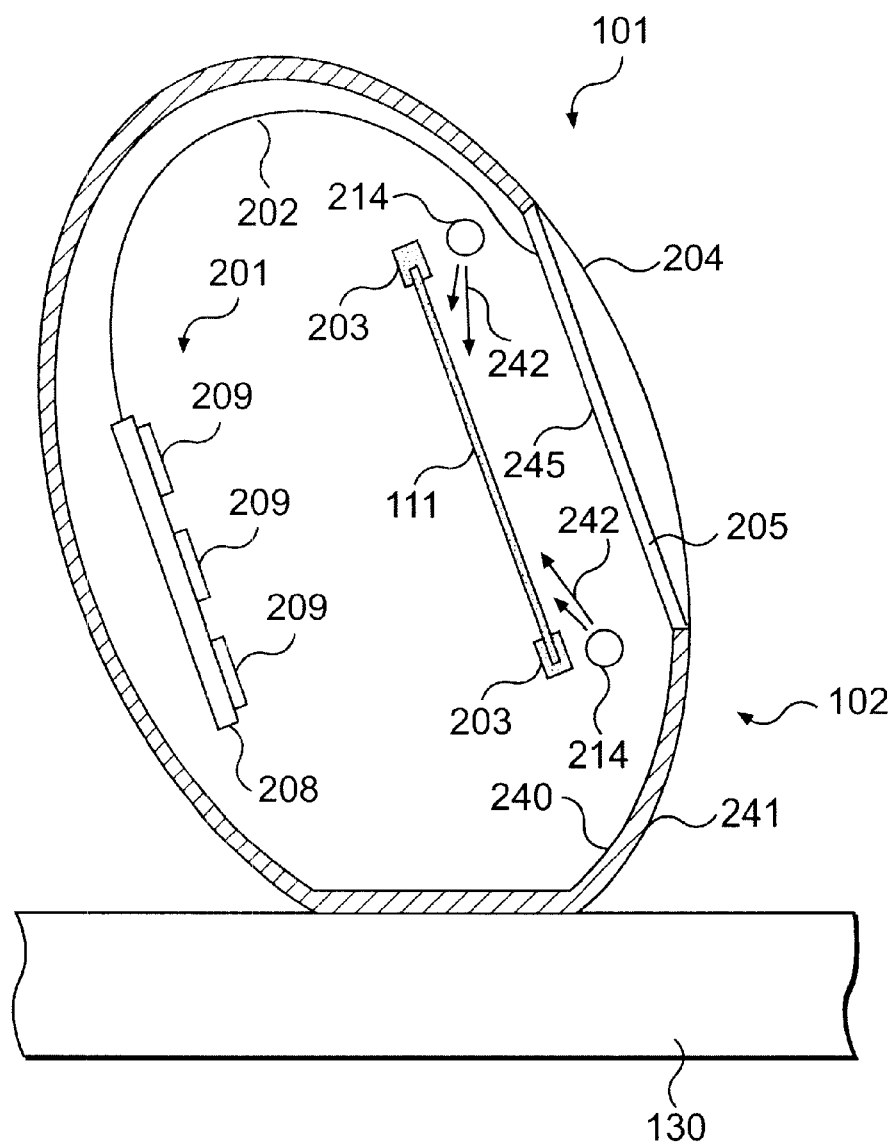
FIG. 2 is a simplified sectional view along line 2—2 of FIG. 1 of an exemplary embodiment of a card scanning system of the present invention.

Referring to FIG. 2 there is shown a simplified sectional view of an information card scanning system 101, as seen from the line 2—2 of FIG. 1, resting on substrate 130. Information card scanning system 101 illustrates several elements, such as electronics 201, an electrical trace or electrical interconnect apparatus 202, brackets 203, optical element 204, and display 205. Additionally, an interior surface 240 and an exterior surface 241 of hollow body 102 is shown in FIG. 2.

Generally, electronics 201 illustrate several elements or features, such as interconnect substrate 208 and integrated circuits 209. Additionally, interconnect apparatus 202 couples electronics 201 and display 205 illustrates, in general, coupling of electronics 201 to various elements or features of information card scanning system 101.

Any suitable interconnect substrate 208, such as a printed circuit board or other suitable circuit board, a silicon interconnect substrate, or the like is usable for interconnect substrate 208. Generally, interconnect substrate 208 provides conductive paths for signals to be routed throughout interconnect substrate 208, as well as enabling signals to be received and transmitted from associated elements of information card scanning system 101, such as sensor system 108, function keys 107, accessory port 122, display 205, brackets 203 and the like. For example, interconnect substrate 208 is coupled to display 205 with interconnect apparatus 202.

Integrated circuits 209 are operably coupled to interconnect substrate 208. Integrated circuits 209 represent a variety electronic components, such as a microprocessor unit (MPU), a memory unit or data storage circuits, as well as standard electronic components, such as resistors, capacitors, and the like. The microprocessor unit includes signal processing circuitry or data processing circuits, as well as logic circuitry that controls or modifies a variety of functions or elements of information card scanning system 101, such as input and output of scanned data, sorting of scanned data, displaying scanned data, driving mechanical features, and the like. Generally, these functions are carried out as software or firmware associated with integrated circuits 209. Coupling of electronics 201 and the various elements or functions of the information card scanning system is achieved by any well-known method in the art, such as electrical coupling, optical coupling, or a combination of both optical and electrical coupling. By way of example, electronics 201 are coupled to display 205 with an electrical or optical cable.

As is shown in FIG. 2, information card 111 is positioned in place by brackets 203. Brackets 203 hold information card 111 in place for direct viewing of information card 111. Additionally, brackets 203 aid in guiding information card past scanning system 108 and into information card scanning system 101, thereby enabling viewing of information card 111 either directly or as an image. Brackets 203 are made using any suitable kind or style, such as mechanical, electromechanical, or the like. Further, brackets 203 have a variety of functions, such as holding information card 111 in position for viewing, moving information card 111 into position for viewing, as well as being equipped with sensors so as to control the position of information card 111.

Optical element 204 includes any suitable optical element well known in the art, such as a transparent film, a refractive optical element, a diffractive optical element, or the like. However, in a preferred embodiment of the present invention, optical element 204 is a refractive optical element or a lens, thereby enabling information card 111 to be viewable in a large format so as to be more easily seen.

A light source 214 is made by any suitable method, such as incandescent light, fluorescent light, electroluminescent light, or the like. Light source 214 is operably coupled to electronics 201 so as to control activity of light source 214. Light source 214 emits light, illustrated by arrows 242, on information card 111, thus enabling the user to directly observe information card 111.

Display 205 is made by any suitable method in the art, such as, but not limited to, liquid crystal display (LCD), vacuum field emission devices (FED), electroluminescent technology, and light emitting diode technology. In a preferred embodiment of the present invention, display 205 uses liquid crystal display technology. The liquid crystal display is made of optically transparent materials, such as glass, polymers, and the like. The optically transparent materials are arranged with electrically conductive paths set out in rows and columns, such that electrical stimulation of a single row and a single column is optically effected to form a pixel. Further, since materials used for display 205 are substantially optically transparent, information card 111 is directly viewable through display 205. Additionally, optimization of viewing of the pixels of display 205 is achieved by having surface 245 of display 205 switchably controlled from substantially optically transparent to substantially optically opaque. Selection of materials used to make display 205 is application specific, thus selection of transparent material is not necessary for the operation of the present invention. Additionally, it should be understood that selecting the appropriate display technology enables information card 111 to be seen as either a real image or a virtual image through display 205.

Figure 3A:
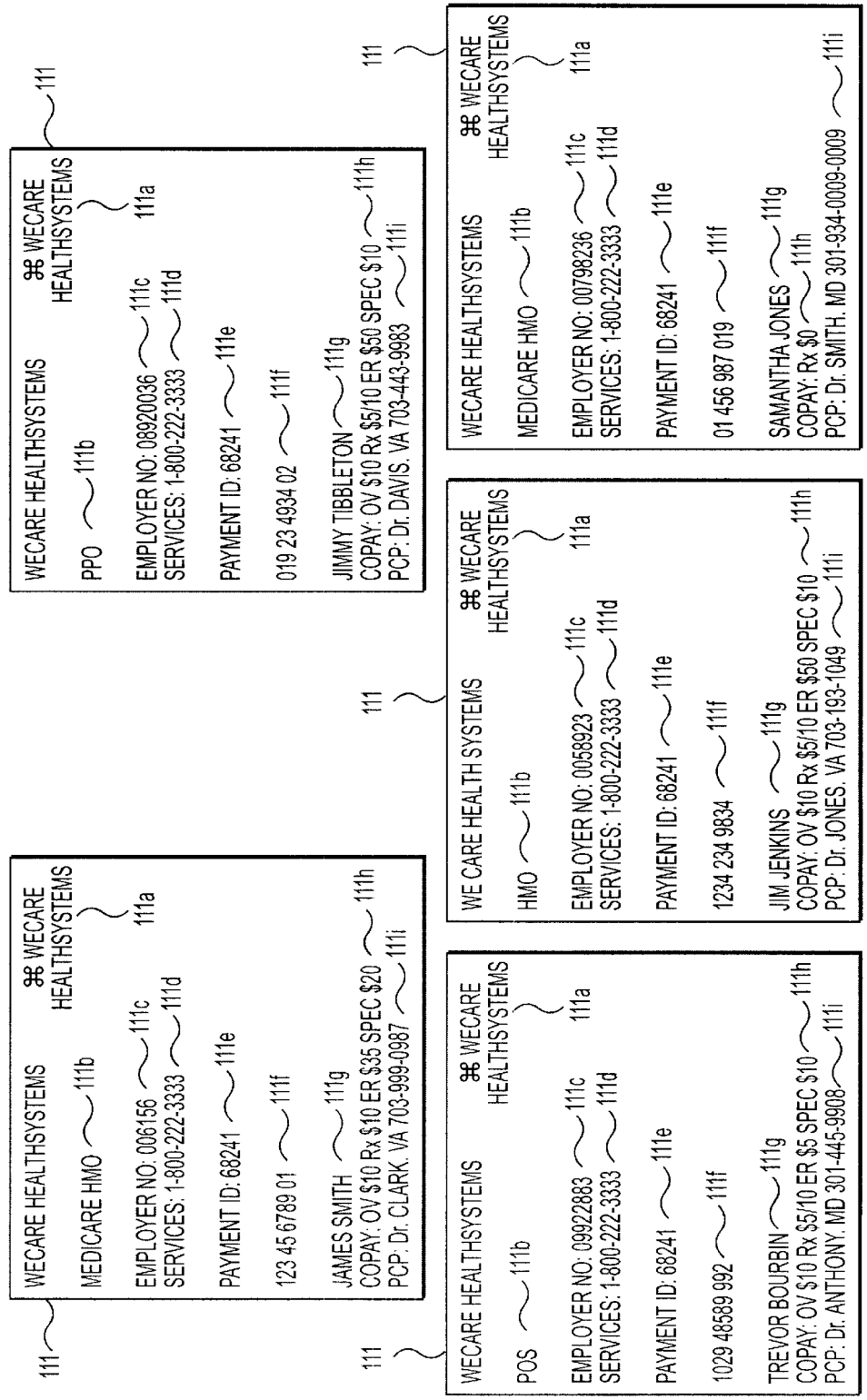
FIG. 3a illustrates exemplary information cards suitable for use in the present invention.

Referring now to FIG. 3a, there are shown several exemplary information cards 111 suitable for use in the present invention. These exemplary cards are shown as being healthcare plan identification cards, or what are alternatively referred to as, insurance cards. Typical healthcare plans can include, but are not limited to, medical, dental, vision care, and pharmacy. It should be apparent to one having ordinary skill in the art that a plurality of information cards, such as, but not limited to, frequent flyer cards, telecommunications cards, rewards cards, or the like can be used in the present invention. Thus, the present invention should not be construed as being limited to the use of insurance cards, or similar media, or the like.

As can be seen in FIG. 3a, information cards 111 include a plurality of information. Exemplary information can include a group identifier 111a. An exemplary group identifier is a healthcare plan identifier, which identifies the healthcare plan sponsor. For the sake of brevity, group identifier or healthcare plan identifier 111a will be referred to herein below as identifier 111a. Identifier 111a preferably includes distinctive textual or graphical data, or both, which can be used to identify the healthcare plan or group with which an individual is related. Identifier 111a generally includes, but is not limited to, the service mark of the healthcare plan sponsor. A group product identifier 111b is also preferably included. An exemplary group product identifier 111b is a healthcare plan product identifier, which identifies the particular healthcare plan product offered by the healthcare plan sponsor in which an individual has chosen to enroll. For the sake of brevity, group product or healthcare plan product identifier 111b, will be referred to herein below as identifier 111b. As shown in FIG. 3a, exemplary healthcare plan products can include, but are not limited to, Medicare HMO, health maintenance organization (HMO), Medicaid HMO, preferred provider network (PPO), and point of service (POS).

An employer number 111c is also included and can identify, for example, an individual's employer so that individual employees can be grouped together based on employer number 111c for reporting functions or the like. Employer number 111c can alternatively be referred to as a group number. A telephone number or a plurality of telephone numbers 111d can also be included to provide telephone contact information to both the cardholder as well as doctor office or pharmacy personnel for a variety of services offered through the healthcare plan.

Also preferably included is a payment identification number 111e that aids in identifying the correct identifier 111a. In an exemplary embodiment, payment identification number 111e permits electronic filing of insurance claims. In the embodiment, the physician's office becomes affiliated with an electronic clearinghouse, such as Electronic Data Systems™ (EDS). The physician's office transmits insurance claim information to the clearinghouse, via, for example, a modem connection or the Internet. The clearinghouse, in turn, uses payment identification number 111e to then forward the claims to the appropriate healthcare plan sponsor for subsequent processing and payment of the claims.

Card 111 also preferably includes an individual identification number 111f which serves to distinctly recognize an individual within the healthcare plan along with the individual's name 111g. Also included on information card 111 is various additional information concerning identifier 111b, such as, but not limited to, copayment amounts 111h and the individual's primary care physician (PCP) 111i. It should be apparent to one of ordinary skill in the art that card 111 may contain additional information to that described herein above.

As shown in FIG. 3b, information is also stored on a second side of card 111. Such information can include patient instructions 111j, physician or facility instructions 111k, telephone numbers or addresses 111l, and a multi-plan identifier 111m, which identifies the healthcare plan for out-of-network services.

Referring now to Table 1, there is shown exemplary group product information. Particularly, Table 1 illustrates exemplary group product information, or what is preferably referred to as healthcare plan product information. This healthcare plan product information preferably includes, but is not limited to, procedures or rules physicians must follow, pertaining to each of the identifiers 111a and 111b described above. The exemplary information shown in Table 1 refers to the services available to an individual when being cared for by a doctor who is recognized as a specialist by the healthcare plan sponsor identified by identifier 111a. It should be apparent to one of ordinary skill in the art, however, that additional information could be included, such as services available from a primary care physician (PCP) or the like.

As can be seen in Table 1, each healthcare plan product (i.e., WeCare Health Systems HMO, WeCare Health Systems Medicare HMO, WeCare Health Systems POS, WeCare Health Systems PPO, and WeCare Health Systems Medicaid HMO) includes a variety of information based upon the particular characteristics of the healthcare plan product. As is known in the art, these plans are generally offered by the healthcare plan sponsors to an individual's employer, for example, and then the individual is given a choice as to which plan he or she wishes to enroll. Exemplary information can include a former name of the plan and a type of plan identifier. Other healthcare plan product information can include a specialist responsibilities section. The specialist responsibilities section identifies any special procedures that a specialist must adhere to when rendering services to an individual, such as but not limited to, the following: rendering treatment per a referral form obtained from the individual's primary care physician (PCP); coordinating care with the PCP; providing reports to the PCP; obtaining referrals from the PCP and authorization from the healthcare sponsor as needed; cooperating with the healthcare sponsor for chart review; and obtaining diagnostic referrals from the PCP. Other information can include copayment information, which may be cumulative to, or in addition to copayment information 111h included on information card 111 (see FIG. 3a). Also included may be any lab referrals required by the healthcare plan sponsor and emergency room guidelines.

TABLE 1

|  | WeCare Health Systems HMO | WeCare Health Systems Medicare HMO | WeCare Health Systems POS | WeCare Health Systems PPO | WeCare Health Systems Medicaid HMO |
|---|---|---|---|---|---|
| Type of Plan | Health Maintenance Organization | Medicare HMO | Point of Service Plan | Preferred Provider Organization | Medicaid HMO |
| Specialist Responsibilities | Render treatment per referral form Coordinate care with PCP Provide reports to PCP Obtain referrals from PCP and authorization | Render treatment for referral form Coordinate care with PCP Provide reports to PCP Obtain referrals from PCP and authorization | Refer patients for diagnostics Extend referrals from PCP as required in manual Provide reports to PCP Obtain authorization | Provide member with information to obtain authorization for out-patient procedures and hospitalizations | Render treatment per referral form Coordinate care with PCP Provide reports to PCP Obtain referrals from PCP and authorization |

TABLE 1-continued

|  | WeCare Health Systems HMO | WeCare Health Systems Medicare HMO | WeCare Health Systems POS | WeCare Health Systems PPO | WeCare Health Systems Medicaid HMO |
| --- | --- | --- | --- | --- | --- |
|  | from Healthcare Plan Sponsor as needed Cooperate with Healthcare Plan Sponsor for reviews Obtain diagnostic referrals from PCP | from Healthcare Plan Sponsor as needed Cooperate with Healthcare Plan Sponsor for reviews Refer to PCP for diagnostic referrals Obtain diagnostic referrals from PCP | from Healthcare Plan Sponsor as needed Cooperate with Healthcare Plan Sponsor for reviews Refer to PCP for additional referrals |  | from Healthcare Plan Sponsor as needed Cooperate with Healthcare Plan Sponsor for reviews Refer to PCP for diagnostic referrals Obtain diagnostic referrals from PCP |
| Copayment Information | Copayment Only | Copayment Only | Copayment only for physician office related service or with referral from PCP Deductible and co-insurance without referral from PCP Coinsurance for out and inpatient procedures/services | Copayment, Deductible and Coinsurance may apply Some services excluded Contact Customer Services for plan specifics either by telephone, fax, or Internet | No copayment |
| Lab Referrals Emergency Room Guidelines | Associated Lab Law permits medical screening in emergent cases. PCP must approve/deny all other treatment. PCP must inform Healthcare Plan Sponsor by calling ER voice mail | Associated Lab Law permits medical screening in emergent cases. PCP must approve/deny all other treatment. PCP must inform Healthcare Plan Sponsor by calling ER voice mail | Associated Lab Unless life threatening PCP should be conferred with my member. Life threatening cases should be authorized by hospital and member by conferring with Healthcare Plan Sponsor management department | Associated Lab Member is responsible for obtaining authorization for emergency room services | Associated Lab Law permits medical screening in emergent cases. PCP must approve/deny all other treatment. PCP must inform Healthcare Plan Sponsor by calling ER voice mail |
| Designated Specialty Networks & Exclusive Arrangements | Gastroenterology: ABD network Radiology: RADIO Network Cardiac Surgery: Mace Hospital Center Physical Therapy: NTR Network Cardiology: NF Network Associates | Gastroenterology: ABD network Radiology: RADIO Network Cardiac Surgery: Mace Hospital Center Physical Therapy: NTR Network Cardiology: NF Network Associates | Radiology: NIM Network Cardiac Surgery: Holt Hospital Center Physical Therapy: NTR Network Cardiology: NF Network Associates | Mental Health: MPH, Inc. Substance Abuse: MPH, Inc. | Gastroenterology: ABD network Radiology: RADIO Network Cardiac Surgery: Mace Hospital Center Physical Therapy: NTR Network Cardiology: NF Network Associates |
| Claims Appeals and Complaints | PaymentIssues: Claims Department PO Box 1221 Boston, MA 31493 800-999-0000 www.wecare.com Medicalreview: Medical Director 2399 Picky Way Oakland, CA 29123 | PaymentIssues: Claims Department PO Box 1221 Boston, MA 31493 800-999-0000 www.wecare.com Medicalreview: Medical Director 2399 Picky Way Oakland, CA 29123 | PaymentIssues: Claims Department PO Box 1221 Boston, MA 31493 800-999-0000 www.wecare.com Medicalreview: Medical Director 2399 Picky Way Oakland, CA 29123 | PaymentIssues: Claims Department PO Box 1221 Boston, MA 31493 800-999-0000 www.wecare.com Medicalreview: Medical Director 2399 Picky Way Oakland, CA 29123 | PaymentIssues: Claims Department PO Box 1221 Boston, MA 31493 800-999-0000 www.wecare.com Medicalreview: Medical Director 2399 Picky Way Oakland, CA 29123 |
| Claims Mailed To: | WeCare Healthcare Systems PO Box 1221 Boston, MA 31493 | WeCare Healthcare Systems PO Box 1221 Boston, MA 31493 | WeCare Healthcare Systems PO Box 1221 Boston, MA 31493 | WeCare Healthcare Systems PO Box 1221 Boston, MA 31493 | WeCare Healthcare Systems PO Box 1221 Boston, MA 31493 |
| Authorization and Preauthorization Guidelines | Referral required for all service outside PCP's office Authorization from Healthcare Plan Sponsor required for all outpatient surgery and hospitalizations | Referral required for all service outside PCP's office Authorization from Healthcare Plan Sponsor required for all outpatient surgery and hospitalizations | In Network: Yes for participating or approved providers Prescript or family form can be used for diagnostic referrals Out of Network: No referral required | No referral forms required Providers should use prescript or facility form for all referral services | All services outside of PCP's office except the following which can be self referred by member to: Certain School Based Health Centers Dental DES Evaluation Family Planning Initial Health assessment for children in State supervised care Mental Health Pregnancy Related Service or women currently receiving prenatal care from non-participating providers Renal Dialysis Pharmacy and Lab (associated with a self |

TABLE 1-continued

| WeCare Health Systems HMO | WeCare Health Systems Medicare HMO | WeCare Health Systems POS | WeCare Health Systems PPO | WeCare Health Systems Medicaid HMO |
|---|---|---|---|---|
| | | | | referral visit only) Substance Abuse Vision |

Additional healthcare plan product information can include designated specialty networks and exclusive arrangements that have previously been negotiated by the healthcare plan sponsor and with which the specialist providing the services to the individual has to adhere. These arrangements can include a plurality of other specialists within the healthcare sponsor network as well as those outside of the network.

Various other information related to the healthcare plan product is provided and includes claims appeals and complaints address information, claim receipt address information, and authorization and preauthorization guidelines. As noted above, additional information could be included. One having ordinary skill in the art should also recognize that each healthcare plan product can have different requirements and or restrictions from the other healthcare plan products.

For example, as shown in Table 1, the Medicaid HMO product does not require a copayment whereas the HMO product does require a copayment. As such, different healthcare plan products will generally have different requirements and these must be followed by the rendering specialist or other physician or dentist, for example, so that the healthcare sponsor or insurance company will cover the individual's expenses and make correct payment to the physician rendering the services.

Figure 4:
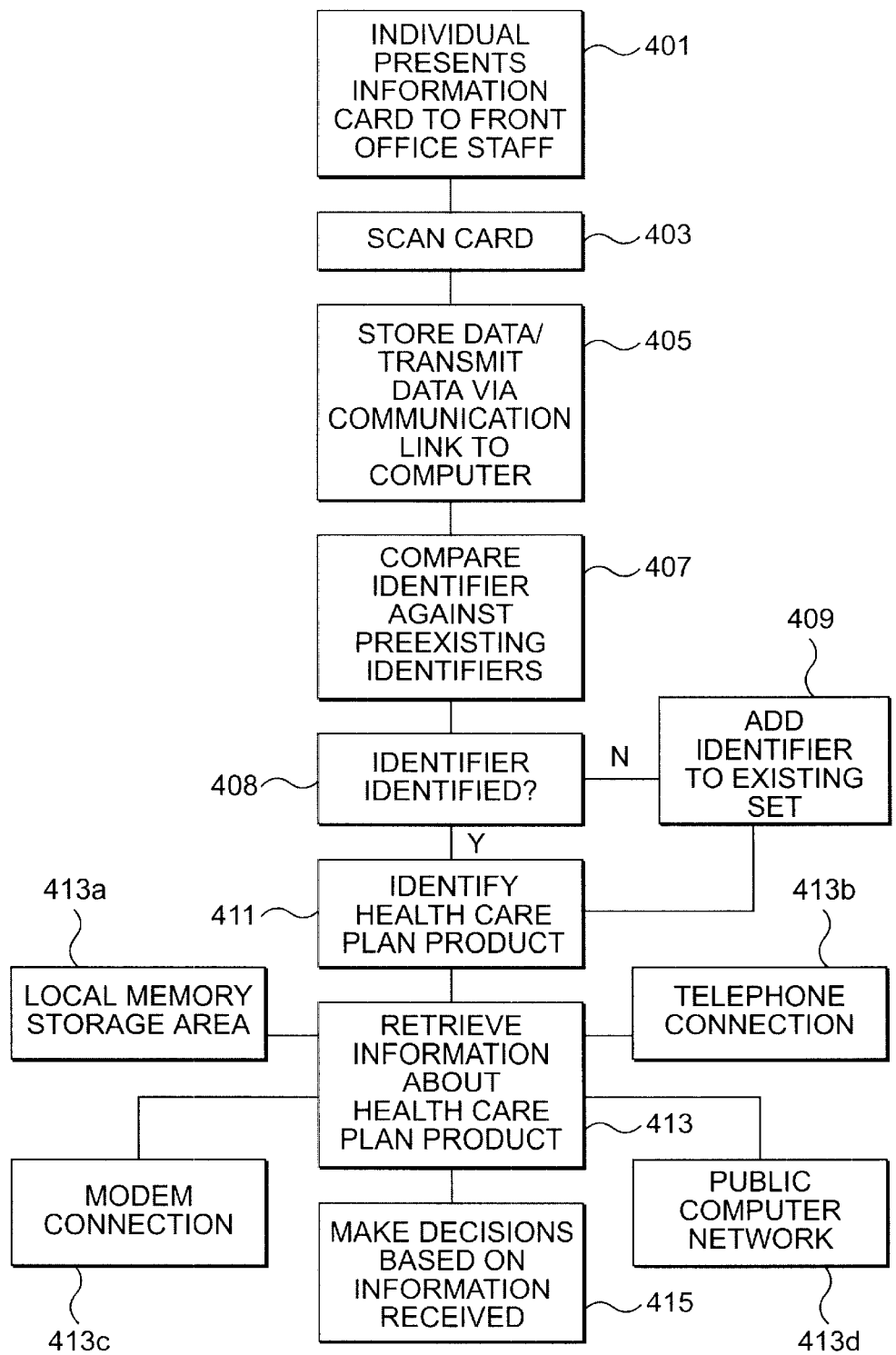
FIG. 4 is an exemplary flow chart showing the operation of the exemplary embodiment of the present invention.

Having described the overall structure and components of an exemplary embodiment of the present invention, focus now turns to the operation of the exemplary embodiment. Referring now to FIG. 4, there is shown an exemplary flow chart showing the operation of the exemplary embodiment of the present invention. As described herein above, when an individual arrives at a doctor or dentist office, the individual will usually present an information or identification card 111 to a member of the front office staff (step 401). In the exemplary embodiment of the present invention, the front office staff member will take information card 111 and place information card 111 into card scanning system 101 as described above. Card scanning system 101 will read the data contained on information card 111 (step 403) and store the data and/or transmit the data via communication link 110 to computer 106 located, for example, at the front office staff members desk (step 405). As noted above with respect to FIG. 3a, the data on information card 111 can include personal information (e.g., name and identification number) which is stored and/or transmitted via communication link 110 to computer 106.

In an alternative exemplary embodiment, the individual can simply state his or her name to the front office staff member. The front office staff member then enters the individual's name into, for example, computer 106, which will access an electronic version of information card 111. As noted above, the electronic version may be stored on computer memory or other type of computer-readable medium, such as, but not limited to, a diskette or CD-ROM. In this embodiment, the information medium is an electronic version or record of the information or identification card.

After the individual's information is accessed by computer 106, the individual can verify that the information is correct. Alternatively, the front office staff member can confirm with the healthcare plan sponsor that the information is correct. This confirmation can be carried out using, for example, a telephone connection or a connection between computer 106 and a server computer located at, for example, the healthcare plan sponsor's facility. Other suitable arrangements, however, could be employed.

In this fashion, the present invention does not require the staff member to enter the data from the information card 111 into computer 106, thereby eliminating entry errors or the like by the staff member. As described above, information card 111 contains at least a group identifier or a healthcare plan identifier 111a. It should be apparent to one of ordinary skill in the art that identifier 111a can correspond to a portion of the data from the information card 111. Identifier 111a is then analyzed to compare identifier 111a against a set of preexisting identifiers preferably located in a memory storage area on computer 106 to identify the particular healthcare plan (step 407).

Identifier 111a could comprise textual data, graphical data, or both textual and graphical data. Where identifier 111a comprises textual data, then the textual data is analyzed in step 407 using, for example, a processor in conjunction with a computer program stored on computer 106, to compare the textual data against the set of preexisting identifiers. Likewise, where identifier 111a comprises graphical data, then the graphical data is analyzed in step 407 using, for example, the processor and computer program stored on computer 106, to compare the graphical data against the set of preexisting identifiers. Finally, where identifier 111a comprises both graphical and textual data, then the graphical and textual data is analyzed in step 407 using, for example, a processor and computer program stored on computer 106, to compare the graphical and textual data against the set of preexisting identifiers.

If a corresponding identifier 111a cannot be identified or identifier 111a is a new identifier (step 408), then the front office staff member will designate the identifier as such and add the identifier, or portion of the data corresponding to identifier 111a on the information card, to the set of preexisting group identifiers in the memory storage area (step 409). This newly added identifier can then be used for future comparisons. It should be apparent to one having ordinary skill in the art that a new identifier may be needed when, for example, the healthcare sponsor changes its service mark or logo, or when the physician joins a new healthcare organization.

Once identifier 111a has been identified and compared, then the individual healthcare plan product is determined based on identifier 111b read from information card 111 (step 411). It should be understood that identifier 111b, like identifier 111a, can comprise textual data, graphical data, or both textual and graphical data and can be analyzed in an analogous method to that described above with respect to identifier 111a. It should also be apparent to one of ordinary skill in the art that identifier 111b can correspond to a portion of the data from the information card 111.

It should be understood by one having ordinary skill in the art that the present invention includes analyzing all or a portion of the data contained on information card 111. Therefore, if only a portion of information card 111 needs to be scanned in order to adequately perform the analysis as described herein, such method is sufficiently within the scope of the present invention.

Using identifier 111b, a processor included on computer 106 retrieves information (step 413), such as the information shown and described above with reference to Table 1, about the healthcare plan product. The information pertaining to the healthcare plan product can be retrieved from a local memory storage area accessed by computer 106 (depicted as step 413a). Alternatively, the information can be obtained by the front office staff member calling the healthcare sponsor and obtaining the information over the telephone (depicted as step 413b). The front office staff member then preferably enters this information into computer 106, using, for example, input device 106b. In a further alternative embodiment, the information can be downloaded via a modem connection between computer 106 and a server computer located, for example, at the healthcare plan sponsor's facilities (depicted as step 413c). In yet a further alternative embodiment, the information can be downloaded via a public computer network, such as, but not limited to, the Internet, to computer 106 (depicted as step 413d). In such an embodiment, the front office staff member would be directed by a hyperlink at, for example, the healthcare sponsor's web site to a page containing the information. It should be understood by one having ordinary skill in the art that the information that is received by any one of steps 413b–413d can be stored on local memory storage area for future reference or, alternatively, on a server computer coupled to computer 106.

Once the information is retrieved by any of the methods described above, then decisions can be made about the individual (step 415). Such decisions can include, but are not limited to, the following: (1) whether the doctor participates in the healthcare product or not; (2) whether a referral is required or not required; (3) what the healthcare product participation allowances are (e.g., what copayments are required for particular services); (4) whether an annual deductible amount is required, and if so, has the individual met the deductible or if the individual must pay a certain amount before reaching the deductible, this can be carried out by the physician's office contacting the healthcare plan sponsor to see what the amount of the remaining deductible; and (5) whether the healthcare product has any special features that the staff member needs to be aware of or the physician needs to be aware of.

Each of these decisions and related information could be presented via computer 106 by any well known method, including but not limited to, a graphical user interface (GUI), a plurality of different screens including information pertaining to each of the exemplary decisions noted above, or graphical text boxes identifying the pertinent information. For example, in an exemplary copay procedure, an instructional text box can be served up on display 106c of computer 106. The instructional text box includes an instruction that a copayment is required for the particular individual. The text box also preferably prompts the staff member to ask for copayment from the individual (e.g., $10 copay for specialist office visit). Once the copayment is received, then the staff member can proceed to enter a payment received notification via, for example, input device 106b. This copayment information can then be entered into a separate billing program.

Moreover, because the information pertaining to the healthcare plan products (see Table 1) generally includes billing correspondence and other types of billing information, automatic invoices or bills can be generated based directly on the information without requiring third-party billing services or the like. Alternatively, although not required, the billing information can be forwarded, either by electronic means or other suitable means, to a third-party billing service or the like. In this fashion, the present invention provides both a stand-alone billing format as well as a seamless integration into existing third party billing formats.

For example, using the individual's personal data contained on the identification card in conjunction with the healthcare plan product information retrieved by the methods described above, bills or invoices can be created for each individual associated with a particular healthcare plan product. Alternatively, a single bill can be generated for each of the individual healthcare plan products which preferably includes all individuals associated with the particular healthcare plan product. It should be understood by one of ordinary skill in the art that any number of suitable billing formats could be used. In yet a further alternative embodiment, the personal data and the healthcare product information can be forwarded to a third party billing service for subsequent billing procedures.

In an exemplary embodiment of a billing system suitable for use in the present invention, a computer program stored on, for example, computer 106 or a server associated with computer 106, can use the individual data and healthcare plan product information to fill in preformatted bills or invoice templates. These bills or invoices can then be forwarded via, for example, postal mail, electronic mail, or facsimile, to the healthcare plan sponsor for payment, or alternatively, to a third party billing service. Alternatively, the bills or invoices can be forwarded electronically over a modem connection or a public computer network connection, such as the Internet, to the healthcare plan sponsor or the third party billing service.

Additional information that can be provided to, for example, a front office staff member or a physician, by the present invention includes, but is not limited to, directing the primary care physician where to transmit referral authorization, directing the specialist where to receive referral authorization, enabling direct import of the information into billing software (see also above), creating directories for insurance filing information, alerting front office staff to special rules, and permitting collection of appropriate copay or coinsurance (i.e., deductible and percentage patient responsibility) amounts.

Computer System

Figure 5:
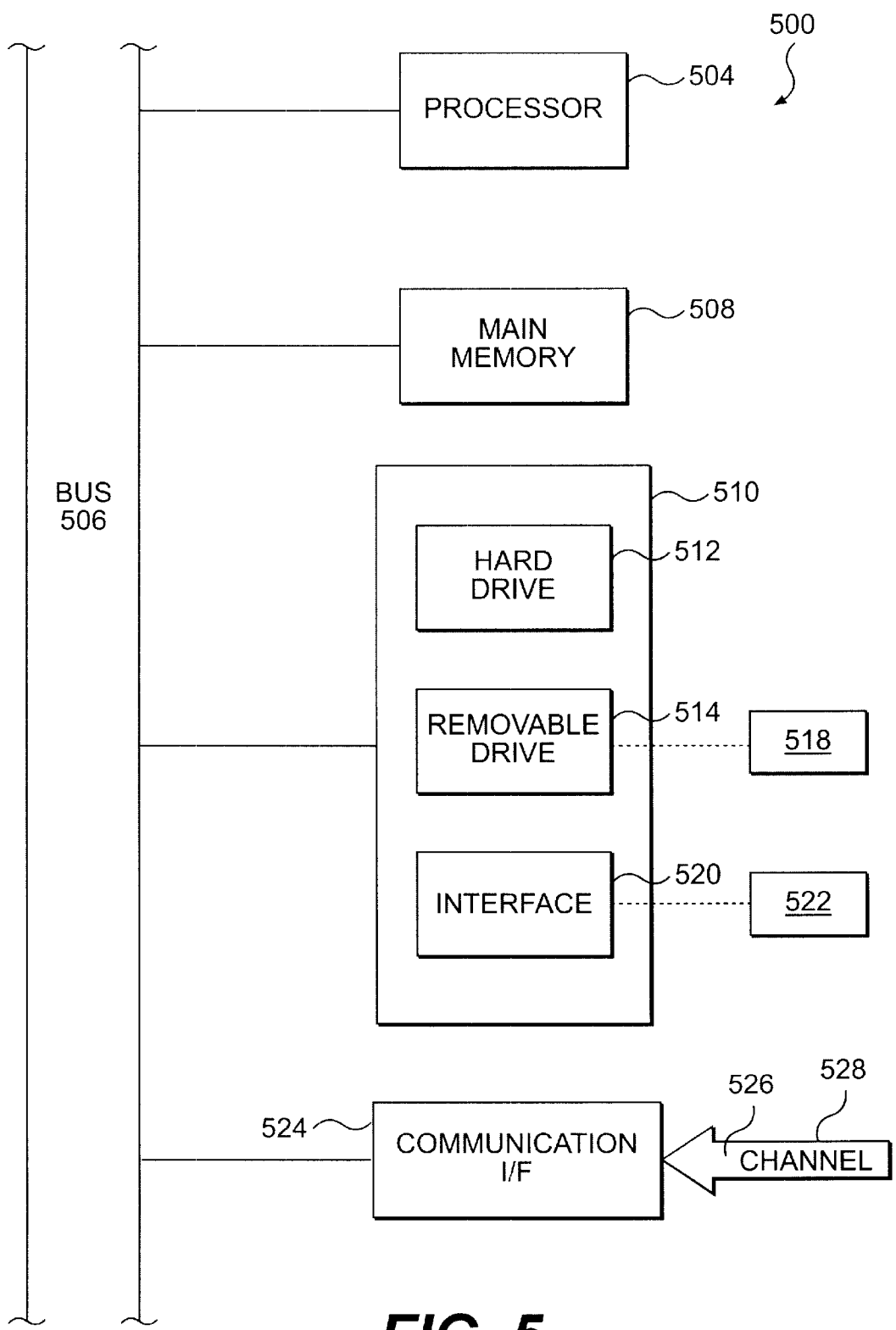
FIG. 5 illustrates a computer system suitable for use in the present invention.

A computer system capable of carrying out the functionality described herein is shown in more detail in FIG. 5. Computer system 500 includes one or more processors, such as processor 504. Processor 504 is connected to a communication bus 506. Various software embodiments are described in terms of this exemplary computer system. After reading this description, it will become apparent to a person skilled in the relevant art how to implement the invention using other computer systems and/or computer architectures.

Computer system 500 also includes a main memory 508, preferably random access memory (RAM), and can also include a secondary memory 510. Secondary memory 510 can include, for example, a hard disk drive 512 and/or a removable storage drive 514, representing a floppy disk drive, a magnetic tape drive, an optical disk drive, etc.

Removable storage drive 514 reads from and/or writes to a removable storage unit 518 in a well known manner. Removable storage unit 518, represents a floppy disk, magnetic tape, optical disk, etc. which is read by and written to by removable storage drive 514. As will be appreciated, removable storage unit 518 includes a computer usable storage medium having stored therein computer software and/or data.

In alternative embodiments, secondary memory 510 may include other similar means for allowing computer programs or other instructions to be loaded into computer system 500. Such means can include, for example, a removable storage unit 522 and an interface 520. Examples of such can include a program cartridge and cartridge interface (such as that found in video game devices), a removable memory chip (such as an EPROM, or PROM) and associated socket, and other removable storage units 522 and interfaces 520 which allow software and data to be transferred from removable storage unit 522 to computer system 500.

Computer system 500 can also include a communications interface 524. Communications interface 524 allows software and data to be transferred between computer system 500 and external devices. Examples of communications interface 524 can include a modem, a network interface (such as an Ethernet card), a communications port, a PCMCIA slot and card, etc. Software and data transferred via communications interface 524 are in the form of signals 526 that can be electronic, electromagnetic, optical or other signals capable of being received by communications interface 524. Signals 526 are provided to communications interface via a channel 528. Channel 528 carries signals 526 and can be implemented using wire or cable, fiber optics, a phone line, a cellular phone link, a RF link and other communications channels.

In this document, the terms "computer program medium" and "computer usable medium" are used to generally refer to media such as removable storage device 518, a hard disk installed in hard disk drive 512, and signals 526. These computer program products are means for providing software to computer system 500.

Computer programs (also called computer control logic) are stored in main memory 508 and/or secondary memory 510. Computer programs can also be received via communications interface 524. Such computer programs, when executed, enable computer system 500 to perform the features of the present invention as discussed herein. In particular, the computer programs, when executed, enable processor 504 to perform the features of the present invention. Accordingly, such computer programs represent controllers of computer system 500.

In an embodiment where the invention is implemented using software, the software may be stored in a computer program product and loaded into computer system 500 using removable storage drive 514, hard drive 512 or communications interface 524. The control logic (software), when executed by processor 504, causes processor 504 to perform the functions of the invention as described herein.

In another embodiment, the invention is implemented primarily in hardware using, for example, hardware components such as application specific integrated circuits (ASICs). Implementation of such a hardware state machine so as to perform the functions described herein will be apparent to persons skilled in the relevant art(s). In yet another embodiment, the invention is implemented using a combination of both hardware and software.

Conclusion

While various embodiments of the present invention have been described above, it should be understood that they have been presented by way of example only, and not limitation. Thus, the breadth and scope of the present invention should not be limited by any of the above-described exemplary embodiments.

What is claimed is:

1. A method for improving patient processing in a medical office, comprising:

scanning at least a portion of an identification card received from a patient to determine a health care plan identifier and a healthcare plan product identifier, wherein each of the health care plan identifier and the healthcare plan product identifier consists essentially of textual data, graphical data, or both textual and graphical data;

comparing via a computer the health care plan identifier to a set of preexisting identifiers stored in a memory storage area;

if the health care plan identifier is not included in the set of preexisting identifiers, adding the health care plan identifier to the set;

retrieving via the computer health care plan product information relating to a health care plan product associated with the health care plan product identifier, wherein the health care plan product information comprises information not available from the identification card, and a plurality of requirements specific to the health care plan product; and displaying to a user in the medical office at least a portion of the health care plan product information.

2. The method of claim 1, wherein the plurality of requirements relate to one or more of specialist responsibilities, referral responsibilities, network guidelines, copayments, deductibles, emergency room guidelines, specialty networks, laboratory guidelines, radiology guidelines, claims appeals, claims address, and authorization guidelines.

3. The method of claim 1, wherein the retrieving step is carried out using a communication link selected from the group consisting of a telephone connection, a modem connection, and a public computer network connection.

4. The method of claim 1, wherein the health care plan identifier includes a textual element and said comparing step comprises comparing the textual element to the set of preexisting identifiers.

5. The method of claim 1, wherein the health care plan identifier includes a graphical element and said comparing step comprises comparing the graphical element to the set of preexisting identifiers.

6. A system for improving patient processing in a medical office, comprising:

a scanner, wherein said scanner is configured to scan at least a portion of an identification card received from a patient to determine a health care plan identifier and a healthcare plan product identifier, wherein each of the health care plan identifier and the healthcare plan product identifier consists essentially of textual data, graphical data, or both textual and graphical data;

a computer system in data communication with said scanner, said computer system comprising a processor configured for comparing the health care plan identifier to a set of preexisting identifiers stored in a memory storage area;

if the health care plan identifier is not included in the set of preexisting identifiers, adding the health care plan identifier to the set;

retrieving health care plan product information relating to a health care plan product associated with the health care plan product identifier, wherein the health care plan product information comprises information not available from the identification card, and a plurality of requirements specific to the health care plan product; and displaying to a user in the medical office at least a portion of the health care plan product information.

7. The system of claim 6, wherein the plurality of requirements relate to one or more of specialist responsibilities, referral responsibilities, network guidelines, copayments, deductibles, emergency room guidelines, specialty networks, laboratory guidelines, radiology guidelines, claims appeals, claims address, and authorization guidelines.

8. The system of claim 6, wherein said computer system comprises a communication port.

9. The system of claim 6, wherein said scanner is an optical scanner.

10. The method of claim 1, wherein the retrieving step is carried out by accessing the memory storage area.

11. The method of claim 1, wherein the retrieving step is carried out by accessing a server coupled to the computer.

12. The method of claim 1, further comprising:

storing at least a portion of the health care plan product information in the memory storage area.

13. The method of claim 1, wherein the retrieving step is carried out using a public computer network connection.

14. The method of claim 13, wherein the health care plan product information comprises information specific to the patient.

15. The method of claim 14, wherein the information specific to the patient relates to a deductible.

* * * * *